United States Patent [19]

Maxson et al.

[11] Patent Number: 5,140,021

[45] Date of Patent: * Aug. 18, 1992

[54] METHOD AND DOSAGE FORM FOR TREATMENT OF PREMENSTRUAL SYNDROME

[75] Inventors: Wayne S. Maxson, Nashville; Joel T. Hargrove, Columbia, both of Tenn.; Philip G. Meyers, Mequon, Wis.

[73] Assignee: Genesis Systems Corporation, Madison, Wis.

[*] Notice: The portion of the term of this patent subsequent to Oct. 16, 2007 has been disclaimed.

[21] Appl. No.: 427,718

[22] Filed: Oct. 27, 1989

Related U.S. Application Data

[60] Continuation of Ser. No. 144,535, Jan. 13, 1988, Pat. No. 4,963,540, which is a division of Ser. No. 851,181, Apr. 14, 1986, abandoned.

[51] Int. Cl.⁵ .................... A61K 31/56; A61K 47/00; A61K 9/66
[52] U.S. Cl. .................... 514/177; 514/786; 424/455
[58] Field of Search .................... 514/177, 522

[56] References Cited

U.S. PATENT DOCUMENTS

| | | | |
|---|---|---|---|
| 2,577,052 | 10/1947 | Himelick | 167/74 |
| 2,675,342 | 9/1950 | Lee et al. | 167/74 |
| 2,988,486 | 6/1961 | Masters et al. | 167/91 |
| 3,051,624 | 8/1962 | Lozinski | 167/74 |
| 3,230,142 | 1/1966 | Spero | 167/55 |
| 3,284,303 | 11/1966 | Meli | 167/74 |
| 3,288,679 | 11/1966 | Fried et al. | 167/74 |
| 3,342,682 | 9/1967 | Erocoli | 167/74 |
| 3,409,721 | 11/1968 | Applezweig | 514/171 |
| 3,535,419 | 10/1970 | Siegrist et al. | 424/22 |
| 3,828,106 | 8/1974 | Rudel | 424/239 |
| 3,862,311 | 1/1975 | Leeson | 424/238 |
| 3,895,103 | 7/1975 | Zaffaroni | 424/22 |
| 4,083,973 | 4/1978 | van der Vies | 260/397.3 |
| 4,177,267 | 12/1979 | Herschler | 424/238 |
| 4,189,102 | 2/1980 | Andrews | 241/5 |
| 4,196,188 | 4/1980 | Besins | 424/37 |
| 4,310,510 | 1/1982 | Sherman et al. | 424/45 |
| 4,381,298 | 4/1983 | Coulson | 424/240 |
| 4,522,831 | 6/1985 | Chatterton, Jr. | 514/169 |
| 4,530,839 | 7/1985 | Pasquale | 514/171 |
| 4,544,544 | 10/1985 | Pasquale | 514/170 |

OTHER PUBLICATIONS

Dennerstein et al., British Medical Journal, vol. 290, Jun. 1, 1985, pp. 1617-1621.
Reid and Yen, Am. J. Obstet. Gynecol., vol. 139, No. 1, pp. 88-104 (1981).
Coulson, Medical Hypotheses, 19:243-255 (1986).
Dalton, J. Steroid Biochem., vol. 20, No. 1, pp. 437-439 (1984).
Lyon et al., Journal of Reproductive Medicine, No. 10, pp. 705-711 (1984).
Maxson et al., Fertility and Sterility, vol. 44, No. 5, pp. 622-626 (1985).
Gonzalez, JAMA Medical News, vol. 245, No. 14 1394-1396 (1981).
Ferre et al., Am. J. Obstet. Gynecol., vol. 148, No. 1, pp. 26-34 (1984).
Whitehead et al., Obstetrical and Gynecological Survey, vol. 36, No. 1, pp. 31-33 (1981).

(List continued on next page.)

Primary Examiner—Frederick E. Waddell
Assistant Examiner—Kimberly R. Jordan
Attorney, Agent, or Firm—Foley & Lardner

[57] ABSTRACT

A pharmaceutical composition suitable for oral administration comprises micronized progesterone in an oil vehicle which is high in glycerides of polyunsaturated fatty acids. Micronized progesterone particles suspended in such an oil vehicle are absorbed more readily into the bloodstream and achieve high progesterone blood serum levels. The pharmaceutical composition according to the invention can be readily formulated into capsules and administered for the treatment of premenstrual syndrome.

12 Claims, 1 Drawing Sheet

OTHER PUBLICATIONS

O'Brien et al., *British Medical Journal,* May 10, 1980, pp. 1161-1163.

Whitehead et al., *British Medical Journal,* Mar. 22, 1983, pp. 825-827.

Sampson, *Brit. J. Pschiat.,* 135:209 at 215 (1979).

Van Der Meer et al., *Journal of Psychosomatic Obstetrics and Gynaecology,* vol. 2, No. 4, pp. 220-222 (1983).

Smith, *Mood and the Menstrual Cycle, Topics in Psychoendocrinology.* Chapter 2, pp. 19-58 (1975).

Morville et al., *J. Gyn. Obst. Biol. Repr.,* 1982, 11, 355-363 (French; includes English abstract).

Ottosson et al., *Acta. Obstet. Gynecol. Scand.,* 63:577-579 (1984).

Lane et al., *British Medical Journal,* vol. 287, pp. 1241-1245 (1983).

Kincl et al., *Journal of Steroid Biochemistry,* vol. 9, pp. 83-84 (1978).

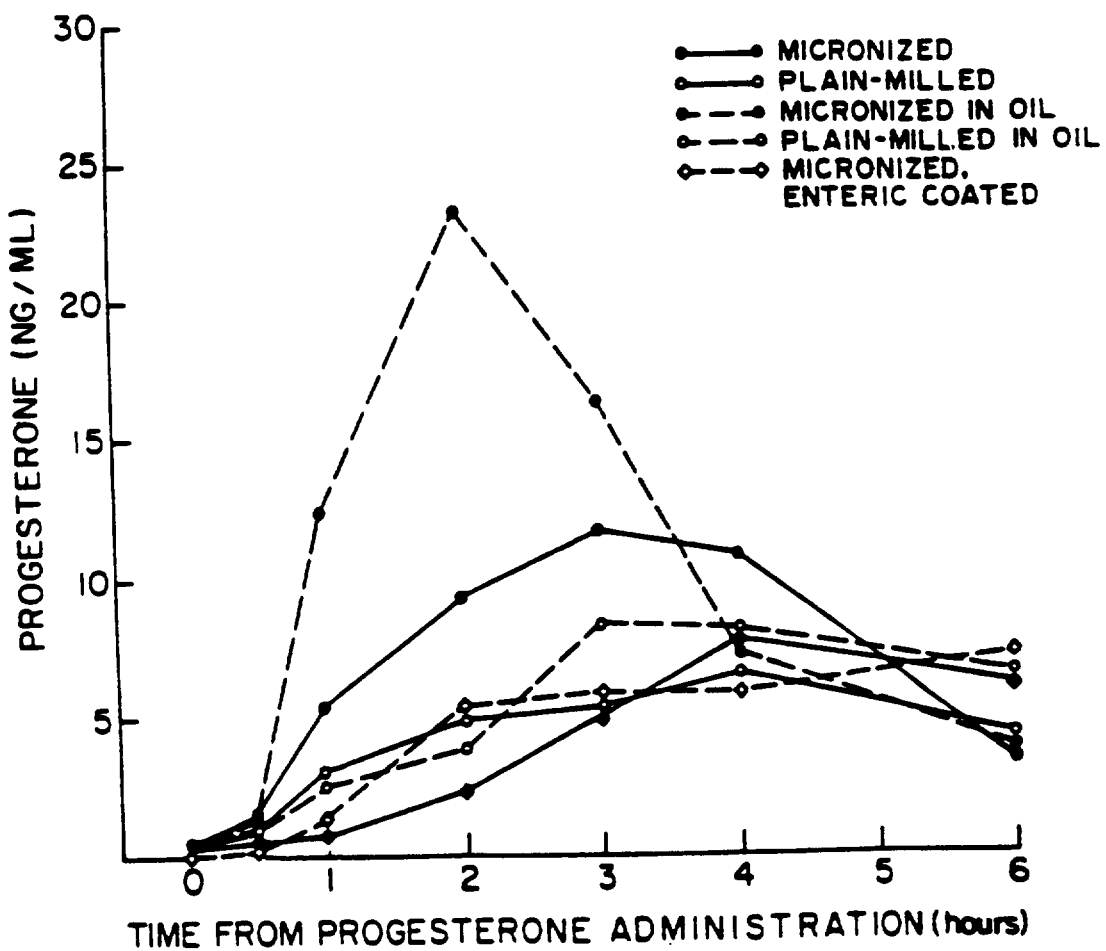

5,140,021

METHOD AND DOSAGE FORM FOR TREATMENT OF PREMENSTRUAL SYNDROME

Which is a continuation of U.S. patent application Ser. No. 07/144,535, filed Jan. 13, 1988 entitled "Method For Treatment of Premenstrual Syndrome", now U.S. Pat. No. 4,963,540, which was a division of U.S. Ser. No. 06/851,181, filed Apr. 14, 1986, abandoned.

FIELD OF THE INVENTION

This invention pertains to a pharmaceutical composition containing progesterone as its active ingredient. The pharmaceutical composition according to the invention is particularly useful for administering progesterone orally to human patients for the treatment of premenstrual syndrome.

BACKGROUND OF THE INVENTION

Progesterone is a naturally occurring steroidal sex hormone also known as Pregn-4-ene-3,20-dione. Progesterone has been used to treat a variety of conditions, including hormonal deficiency of the corpus luteum. The present invention concerns a new dosage form of progesterone particularly suitable for the treatment of premenstrual syndrome.

A wide variety of pharmeceutical compositions containing progesterone and a carrier or vehicle for progesterone have been proposed. The following patents, for example, disclose a variety of compositions containing progesterone, progesterone derivatives or other steroids in a wide variety of carriers or vehicles: Himelick U.S. Pat. No. 2,557,052 issued Jun. 12, 1951, Lee U.S. Pat. No. 2,675,342 issued Apr. 13, 1954, Masters U.S. Pat. No. 2,988,486 issued Jun. 13, 1961, Lozinski U.S. Pat. No. 3,051,624 issued Aug. 28, 1962, Spero U.S. Pat. No. 3,230,142 issued Jan. 18, 1966, Ercoli U.S. Pat. No. 3,342,682 issued Sep. 19, 1967, Rudel U.S. Pat. No. 3,828,106 issued Aug. 6, 1974, van der Vies U.S. Pat. No. 4,083,973 issued Apr. 11, 1978, Herschler U.S. Pat. No. 4,177,267 issued Dec. 4, 1979, Hussain U.S. Pat. No. 4,383,993 issued May 17, 1983, Sherman U.S. Pat. No. 4,310,510 issued Jan. 12, 1982, Fried U.S. Pat. No. 3,288,679 issued Nov. 29, 1966, Siegrist U.S. Pat. No. 3,535,419 issued Oct. 20, 1970, Coulson U.S. Pat. No. 4,381,298 issued Apr. 26, 1983, Applezweig U.S. Pat. No. 3,409,721 issued Nov. 5, 1968, Pasquale U.S. Pat. No. 4,530,839 issued Jul. 23, 1985, Pasquale U.S. Pat. No. 4,544,554 issued Oct. 1, 1985, Chatterton, Jr. U.S. Pat. No. 4,522,831 issued Jun. 11, 1985 and Royer U.S. Pat. No. 4,349,530 issued Sep. 14, 1982. The following patents particularly concern compositions for administering progesterone orally: Meli U.S. Pat. No. 3,284,303 issued Nov. 8, 1966, Leeson U.S. Pat. No. 3,862,311 issued Jan. 21, 1975, Besins U.S. Pat. No. 4,196,188 issued Apr. 1, 1980. The foregoing patent to Besins is particularly pertinent to the present invention insofar as it discloses a dosage form comprising capsules containing micronized progesterone in an oil vehicle.

It has long been recognized that oral administration of progesterone involves certain difficulties. For example, as described in the foregoing patents to Meli and Rudel, progesterone taken orally is absorbed in the small intestine but thereafter exhibits relatively progestational activity. Progesterone circulated through the liver is metabolized into other, inactive compounds. Progesterone is described as having a short "half-life" in the blood.

An essential problem in the treatment of premenstrual syndrome (PMS) is the administration of sufficient progesterone to increase the level in the blood to at least 10–12 nanograms per milliliter (ng/ml). A blood serum level in the range of 12 to 20 ng/ml is particularly desirable, since this is the normal level that occurs during the menstrual cycle.

In practice, it has proven very difficult to provide an oral formulation of progesterone which reaches and sustains a high blood serum progesterone level. The composition taught by the foregoing patent to Besins employs micronized particles of recrystallized progesterone. In the preferred embodiment of Besins, at least 80% of the particles preferably have a particle size in the range of from 5 to 15 microns. These particles are micronized in oil.

The present invention provides an orally administrable form of progesterone which, like the Besins composition, can be used to fill capsules, but is more easily prepared than the Besins composition. The pharmaceutical composition according to the present invention also exhibits an unusually high activity as reflected by both the peak level of progesterone blood serum concentration and the length of time a high blood serum concentration of progesterone is maintained after the composition is administered orally.

SUMMARY OF THE INVENTION

This invention provides a pharmaceutical composition containing micronized progesterone and an edible, pharmcologically acceptable oil high in unsaturation, particularly in polyunsaturation. The micronized progesterone particles are suspended in the oil vehicle, which may have progesterone dissolved therein. The highly unsaturated oil comprises mainly glycerides of fatty acids. A major part (e.g. at least 51 percent by weight) of these glycerides are glycerides of polyunsaturated fatty acids, particularly of dienoic acids such as linoleic acid.

The present invention further provides a method for the treatment of premenstrual syndrome (PMS) which comprises administering to a woman an effective dosage of the pharmaceutical composition according to the invention.

BRIEF DESCRIPTION OF THE DRAWING

The drawing is a graph showing progesterone blood serum level, measured in nanograms per milliliter, versus time in hours, for several types of oral progesterone formulations.

DETAILED DESCRIPTION

This invention provides an effective oral dosage form for progesterone containing two essential ingredients. The first ingredient is progesterone, the active ingredient in the pharmaceutical composition according to the invention. Progesterone can be isolated from natural sources such as the corpus luteum of animals, or produced synthetically. See, for example, U.S. Pat. No. 2,379,832, the contents of which are incorporated by reference herein. Progesterone is presently available commercially (U.S.P. Progesterone).

The pharmaceutical composition according to the invention contains progesterone which has been micronized, i.e. the individual progesterone particles in the powder have been reduced in size to a few microns in diameter, or in the case of non-round particles, to a few microns in their largest dimensions. As used herein, the term "micronized progesterone" refers to a powdered progesterone product wherein the particle size of virtually all (at least 99%) of the progesterone particles is less than about 25 microns.

The Besins patent cited above preferably employs micronized progesterone particles of which at least 80% of the particles have a particle size of from 5 to less than about 15 microns. Besins teaches that micronized progesterone having a particle size of 5 microns loses a great part of its activity after being stored for three months (See Besins Table 3). By contrast, the pharmaceutical composition of this invention can achieve excellent blood serum progesterone levels in humans, even after up to 6 months storage, using micronized progesterone having smaller particle sizes than the micronized particles preferred in the Besins patent.

In the preferred micronized progesterone of this invention, virtually all (99%) of the progesterone particles have particle sizes of less than 10 microns, and a majority (e.g. 78%) of these particles have particle sizes of less than 5 microns. Micronized progesterone products of this type are available from Berlichem, a division of Schering AG, and from the Upjohn Company. Micronized progesterone can be prepared from bulk progesterone in a radiator mill (jet air micronizer). The following U.S. patents disclose micronization techniques and machines, and are incorporated Feb. 19, 1980, Andrews U.S. Pat. No. 2,032,827 issued Mar. 3, 1936, Andrews U.S. Pat. No. 4,018,388 issued Apr. 19, 1977. The micronized progesterone projects made by Upjohn and Berlichem can be used in the present invention without difficulty. In particular, the difficulties with the hygroscopic and electrostatic properties of micronized progesterone described by Besins do not inhibit the practice of the present invention.

The second major component of the present invention is an oil which serves as a vehicle for the micronized progesterone. The composition and properties of the oil employed as the vehicle have a large effect on the effectiveness of the product. Oils high in glycerides of polyunsaturated fatty acids are particularly effective for purposes of the present invention. Such polyunsaturated fatty acids include linoleic, linolenic, santalbic, eleostearic, punicic, trichosanic and parinaric acids. Of the foregoing acids, linoleic and linolenic acids are particularly common in natural vegetable oils. Accordingly, the oily vehicle according to the present invention is preferably a natural vegetable oil consisting mainly of glycerides of fatty acids, wherein the fatty acid glycerides comprise 51 to 95 weight percent of glycerides of polyunsaturated fatty acids, particularly 70 to 80 weight percent of glycerides of polyunsaturated fatty acids. Such natural vegetable oils include, for example, safflower oil, linseed oil, soybean oil, corn oil and sunflower oil. Mixtures of these and other vegetable oils having similar properties can also be employed.

The total unsaturation of an oil is indicated by its iodine value (IV). The oil vehicle according to the present invention preferably has an iodine value of at least 110, particularly 130-160, most preferably 140-150. The iodine values of the foregoing oils are approximately as follows: Safflower oil, 130-150; linseed oil, 175-190; soybean oil, 128-137; corn oil, 109-133; sunflower oil, 113-143, Peanut oil has an IV of about 90-97.

Safflower oil has proven particularly effective as an oil vehicle for the pharmaceutical composition of this invention. The properties of safflower oil are as follows:

TABLE 1

| Properties of Safflower Oil | | |
|---|---|---|
| | Broad Range | Preferred Range |
| Acid Value | 0.4-10 | 1.0-9.7 |
| Saponification Value | 186-194 | 188-194 |
| Iodine Value | 130-150 | 140-150 |
| Thiocyanogen Value | 82-87 | 82.5-86 |
| R-M (Reichert-Meissl) Value | less than 0.5 | 0.1-0.5 |
| Hydroxyl Value | 1-12 | 2.9-6.0 |
| Unsaponifiable (%) | less than 1.5 | 0.3-1.3 |
| Specific Gravity, 25/25° C. | 0.919-0.924 | 0.919-0.924 |
| Refractive Index, nD, 25° C. | 1.472-1.476 | 1.473-1.475 |
| Refractive Index, nD, 40° C. | 1.467-1.470 | 1.4690-1.4692 |
| Titer | 15-18 | 15-18 |

An edible oil having most or all of its properties in the foregoing ranges is particularly preferred for use in the present invention.

The following table gives approximate oil compositions of several typical vegetable oils:

TABLE 2

| Oil Compositions (in wt. % of total glycerides) | | | | |
|---|---|---|---|---|
| Glycerides of Fatty Acids | Safflower | Linseed | Soybean | Peanut |
| Saturated (all kinds)* | 5-10 | 5.9-16 | 14-14.2 | 15.5-21.9 |
| Unsaturated | | | | |
| Oleic (1) | 13.4-21.1 | 13-28.6 | 22.9-26.1 | 42.3-71.5 |
| Linoleic (2) | 72.9-79 | 15.2-22.4 | 49.2-49.6 | 13.0-33.4 |
| Linolenic (3) | up to 0.13 | 47.3-54 | 7.9-10.7 | — |
| Others | — | up to 0.4 | — | 0.9-2.4 |

*Includes primarily palmitic, stearic, arachidic, behenic, lignoceric, and myristic acids. Typical breakdown for safflower oil: palmitic 6.4 wt %, stearic 3.1 wt %, arachidic 0.2 wt %.
(1) Unsaturated with one double bond, 9-Octadecandic acid
(2) Unsaturated with two double bonds, 9, 12-Octadeadienoic acid
(3) Unsaturated with three double bonds, 9,13,15-Octadecatrienoic acid As the foregoing table suggests, the oil used as the oily vehicle according to the present invention usually contains not more than about 16 weight percent glycerides of saturated fatty acids, particularly not more than about 10 weight percent glycerides of saturated fatty acids.

The pharmaceutical composition of this invention is particularly adapted for filling capsules, particularly soft gelatin capsules, so as to make an oral dosage form which can be stored (preferably refrigerated) and then taken as needed. Although the effective amount of progesterone per capsule can vary widely, in accordance with the nature of the capsules and the needs of the patient, a dosage of from 50-150 milligrams per capsule, particularly 90-110 milligrams progesterone per capsule, is preferred. The oil vehicle is used in an amount ranging from 1.5-2.5 milliliters of the oil per one gram of the progesterone. To make a batch of capsules, typically 400 milliliters of the oil is mixed with about 200 grams of progesterone. If the oil:progesterone ratio exceeds 2.5 ml/g by very much, the total size of the capsule is too large, in other words, it would take too large a capsule to contain the oil:progesterone mixture containing 100 mg progesterone. If the oil:progesterone ratio is much below 1.5 ml/g, the resulting suspension is too thick.

The method of treating PMS according to the present invention generally involves administering progesterone orally to a woman in order to increase her blood serum progesterone concentration during the menstrual cycle. In a male or in a woman during the first half of the menstrual cycle, the progesterone blood serum concentration normally ranges between 0.3 ng/ml and 1.0 ng/ml. After ovulation in the woman, the progesterone level generally rises to greater than 3 ng/ml, often reaching an average of 10-15 ng/ml in the middle part of the second half of the menstrual cycle. The present inventors have found that increasing the blood serum level of progesterone to at least 10-12 ng/ml, particularly 12-20 ng/ml, is important in treating PMS.

Treatment of PMS according to the present invention generally involves administration of 200-600 milligrams of progesterone per patient per day, although larger or smaller effective amounts could be employed in individual cases. In general, when the daily dosage exceeds 600 milligrams per day, the treatment has an undesirable sedative effect. A dosage of less than 200 milligrams per day is generally insufficient to increase the level of progesterone in the blood to the desired level. A typical treatment, for example, would involve administration of 300 mg daily, in the form of one capsule containing 100 milligrams micronized progesterone according to the invention, three times per day.

A typical treatment plan according to the method of this invention is as follows. Assuming a 28 day menstrual cycle in which ovulation occurs on day 14, the woman patient suffering from PMS takes capsules according to the invention containing 100 mg progesterone 3 times per day for 12 consecutive days, beginning on day 16. The increased blood progesterone level the patient has due to this treatment effectively mitigates or eliminates the PMS symptoms.

The following examples illustrate the preparation of an oral dosage form of the pharmaceutical composition according to the invention, and subsequent tests showing the enhanced effectiveness of the composition according to the invention in comparison to comparable progesterone dosage forms.

PREPARATION EXAMPLE

Micronized progesterone was made according to the Berlichem method as follows. The jet air pulverizer used was a Spiral-Mill (fluid energy mill) manufactured by Schering, AG, West Germany. Milling occurs due to a strong continuous acceleration and deceleration of the feed stock by expanding nitrogen gas within the cylindrical milling chamber. Collisions occur constantly between the particles, resulting in comminution. A cyclone separator is used to internally classify the material. The finest particles leave the milling chamber through a central outlet, whereas the larger particles continue circling in the mainstream around the periphery. The fineness of the micronized material is controlled by adjusting the feed rate, milling gas pressure, and the angle of the gas jets. The charge rate of the mill is about 50 kilograms progesterone per hour, and the air speed in the mill is about 300-500 meters per second. Due to the high air speed, the progesterone is in the mill for a period of time measured only in milliseconds or seconds, e.g., not more than about 10 seconds, depending on the particle size of the starting material (feed stock).

Berlichem micronized progesterone (200 grams) consisting of 78% of particles having particle sizes less than 5 microns and 99% of particles having particle sizes of less than 10 microns, made according to the foregoing method, were mixed with 400 ml of safflower oil at room temperature. The resulting mixture was further mixed in a Eyela D.C. Stirrer DC-RT with a jacket heated to 24 degrees centigrade for 15-30 minutes at a maximum rpm of 200. Upon completion of mixing, No. 3 plain gelatin capsules were filled using conventional capsule filling apparatus to prepare the oral dosage form of progesterone according to the invention. Each capsule contained 100 mg of progesterone.

TEST EXAMPLES

A variety of samples designated A through Z below were prepared in order to illustrate the improved effectiveness of the pharmaceutical composition according to the invention. Samples B, J, K, L, O, V and X represent the invention. The other samples were tested for purposes of comparison.

For samples D, E and N, plain milled progesterone was employed in place of micronized progesterone as described in the preceding preparation example. Such milled progesterone typically comprises particles having particle sizes of about 40-50 microns.

For samples C, H, I, M, P, Q, R and S, the oil vehicle was a comparative vehicle, such as mineral oil, carnuba wax, an enteric coating consisting essentially of stearic acid and carnuba wax, and ordinary vegetable cooking oil (Crisco oil, made of partially hydrogenated soybean oil, polysorbate 80, and polyglycerol esters).

For samples F, T, W and Y, the pharmaceutical composition according to the invention was replaced with Utrogestan, a French product from Laboratories Besins containing 100 milligrams of progesterone per capsule. For samples G, H, V and Z, progesterone was dissolved (instead of suspended) in the vehicle by heating the resulting mixture until the progesterone was dissolved. For safflower oil, heating to 81° C. was necessary to dissolve the progesterone. Except for the samples comprising Utrogestan, each sample was prepared using the procedure of the foregoing preparation example, except as otherwise specifically noted below.

Sample K according to the invention involved a special procedure. First, 24 mg of Berlichem micronized progesterone were dissolved on 0.2 ml safflower oil by heating the mixture to about 81° C. The progesterone was thereby dissolved, and the resulting solution was allowed to cool to room temperature. Then, 26 mg of Berlichem micronized progesterone was suspended in the oil solution at room temperature. The resulting suspension was then filled into a No. 3 plain gelatin capsule.

The subjects for blood progesterone level tests were 10 women and 2 men. The women are designated F1 to F10, respectively, and the two men are designated M1 and M2. The following table summarizes the subjects for each test and the composition administered to those subjects:

TABLE 3

| Sample | Subject(s) | Composition (active indigient, vehicle) |
|---|---|---|
| A (comparison) | F1-F6, M1 | Micronized progesterone* (Upjohn) no vehicle |
| B (invention) | F1-F6, M1 | MP (Upjohn) safflower oil |
| C (comparison) | F1-F6, M1 | MP (Upjohn) enteric coated |
| D (comparison) | F1-F6, M1 | Milled progesterone (Upjohn) no vehicle |
| E (comparison) | F1-F6, M1 | Milled progesterone (Upjohn) in |

The following Table 4 summarizes the results for samples A-E:

TABLE 4

|  | Sample | | | | |
| --- | --- | --- | --- | --- | --- |
|  | A | B | C | D | E |
| Number of repetitions | 14 | 7 | 7 | 7 | 7 |
| Peak serum progesterone level in ng/ml | 13.2 ± 2.4* | 30.3 ± 7.0 | 11.2 ± 3.0 | 9.6 ± 2.5 | 11.3 ± 3.0 |
| Time to peak serum progesterone level, in hours | 3.2 ± 0.4 | 2.0 ± 0.3 | 4.1 ± 0.7 | 4.0 ± 0.5 | 4.1 ± 0.5 |

*Uncertainties indicated are one standard deviation

| Sample | Subject(s) | Composition (active indigient, vehicle) |
| --- | --- | --- |
| | | safflower oil |
| F (comparison) | M2 | MP in oil (Besins Utrogestan, 100 mg progestrone per capsule) |
| G (comparison) | M2 | 96 mg MP (Upjohn) heat dissolved in safflower oil |
| H (comparison) | M2 | MP (Upjohn) heat dissolved in mineral oil |
| I (comparison) | M2 | MP (Upjohn) suspended in vegetable soybean cooking oil (Crisco, registered trademark of Proctor and Gamble Co.) |
| J (invention) | M2 | MP (Berlichem) in safflower oil |
| K (invention) | M2 | MP in safflower oil, 24 mg. heat dissolved, 76 mg. suspended at room temp. |
| L (invention) | M2 | MP (Upjohn) in safflower oil |
| M (comparison) | M2 | MP (Upjohn) in mineral oil |
| N (comparison) | M2 | Plain milled U.S.P. progesterone in safflower oil |
| O (invention) | M2 | MP (Berlichem) in linseed oil |
| P (comparison) | F7 | MP in carnauba wax |
| Q (comparison) | M2 | MP in equal parts of carnauba wax and safflower oil |
| R (comparison) | M2 | MP in equal parts of stearic acid and safflower oil |
| S (comparison) | F7 | Equal parts of MP in safflower oil and in stearic acid, in admixture |
| T (comparison) | F8 | Utrogestan |
| U (comparison) | F8 | 96 mg MP heat dissolved in safflower oil |
| V (invention) | F8 | MP in safflower oil |
| W (comparison) | F9 | Utrogestan |
| X (invention) | F9 | MP in safflower oil |
| Y (comparison) | F10 | Utrogestan |
| Z (comparison) | F10 | 96 mg MP heat dissolved in safflower oil |

*MP = Micronized progesterone

Blood samples were drawn from each subject in order to establish the starting progesterone blood level. Each subject then received one or two capsules containing the progesterone and vehicle. Each such capsule contained 100 milligrams of progesterone, with the exception of capsules prepared for Samples G and U which contained 96 milligrams progesterone. After progesterone administration, blood was drawn at 0.5, 1, 2, 3, 4, 6 and 24 hours thereafter. Blood serum was separated by centrifugation, labeled, and subsequently assayed for progesterone. The progesterone assay was performed by solid phase, unextracted radioimmunoassay using a kit obtained from Diagnostic Products Corporation, Los Angeles, Calif. Interassay variation was about 4.3 percent, and intraassay variation was about 7.5 percent, as measured for samples A through E. The resulting blood serum levels of progesterone were measured in nanograms per milliliter (ng/ml), and are so indicated in the tables below which summarize the results.

The patients taking capsules according to Samples A-E took two capsules for each trial, for a total effective dosage of 200 mg progesterone. For Samples F-Z, each patient took only one capsule each for a total dosage of 100 or 96 mg progesterone.

The results given in Table 4 demonstrate a synergistic improvement in peak blood serum progesterone level achieved by employing micronized progesterone together with highly unsaturated vegetable oil (safflower oil). Outstanding results were obtained using the composition of Sample B, wherein micronized progesterone was used in safflower oil. The results for Sample B are synergistic as compared to samples A, D and E; in other words, the improvement in peak serum progesterone level using micronized progesterone and safflower oil together was greater than the sum of the marginal improvements obtained using micronized progesterone without a vehicle, or using plain milled progesterone is safflower oil. These results demonstrate that the pharmaceutical composition according to the invention is remarkably and unexpectedly effective in both its peak serum progesterone level and the short time needed to reach this level.

The drawing illustrates results of further trials conducted according to substantially the same procedures as described for Table 4. Like the results presented in Table 4, the drawing graphically illustrates that the progesterone serum level for the curve labeled "micronized in oil", namely, micronized progesterone in safflower oil, was distinctly superior to the various other combinations of micronized progesterone with no vehicle, plain milled progesterone with no vehicle, plain milled progesterone in safflower oil, and plain milled progesterone with an enteric coating. Such results are believed to demonstrate that the pharmaceutical composition according to the present invention is remarkably more effective than similar progesterone formulations for increasing the blood serum level of progesterone in a human being over a longer period of time.

The following Table 5 illustrates the effectiveness of the composition according to the invention in comparison to similar products using other oils:

TABLE 5

| | SAMPLES | | | | | | | | | |
| --- | --- | --- | --- | --- | --- | --- | --- | --- | --- | --- |
| | | F | G | H | I | J | K | L | M | N | O |
| Time (after administration, in hours) | 0 | 0.5 | 0.3 | 0.3 | 1.3 | 0.6 | 1.1 | 0.6 | 1.0 | 0.3 | 0.4 |
| | ½ | 0.5 | 0.9 | 0.6 | 1.1 | 0.3 | 7.5 | 0.6 | 0.8 | 0.3 | 0.4 |
| | 1 | 0.7 | 1.3 | 0.5 | 1.3 | 0.7 | 23.8 | 0.7 | 1.8 | 0.4 | 0.8 |
| | 2 | 1.4 | 1.5 | 0.5 | 1.4 | 18.6 | 5.6 | 8.7 | 6.5 | 2.0 | 4.4 |
| | 3 | 2.8 | 1.6 | 0.9 | 1.5 | 4.7 | 3.3 | 8.2 | 6.2 | 3.1 | 10.2 |
| | 4 | 9.2 | 1.3 | 1.4 | 6.5 | 6.0 | 2.6 | 3.2 | 3.4 | 3.4 | 4.8 |
| | 6 | 3.5 | 1.9 | 1.2 | 6.5 | 2.2 | 2.5 | 3.0 | 3.1 | 2.9 | 2.1 |
| | 24 | 0.9 | 0.7 | 0.3 | 1.0 | 1.5 | 1.0 | 0.9 | 0.7 | NM | NM |
| Peak serum progesterone | | 9.2 | 1.6 | 1.4 | 6.5 | 18.6 | 23.8 | 8.7 | 6.5 | 3.4 | 10.2 |

TABLE 5-continued

| | SAMPLES | | | | | | | | | |
|---|---|---|---|---|---|---|---|---|---|---|
| | F | G | H | I | J | K | L | M | N | O |
| level in ng/ml | | | | | | | | | | |
| Hour peak serum level reached | 4 | 3 | 4 | 4 | 2 | 1 | 2 | 2 | 4 | 3 |

NM = Not measured

The results summarized in the bottom two lines of Table 5 indicate that the samples according to the present invention, particularly samples J, K and O, achieved higher peak serum levels in shorter times than any of the comparative samples employing various combinations of carnuba wax, safflower oil and stearic acid as vehicles:

TABLE 6

| | | Sample | | | |
|---|---|---|---|---|---|
| | | P | Q | R | S |
| Time (after administration, in hours) | 0 | 0.1 | 0.2 | 0.3 | 0.4 |
| | ½ | 0.1 | 0.4 | NM | NM |
| | 1 | 0.1 | 0.3 | NM | NM |
| | 2 | 0.2 | 2.4 | 8.0 | 0.7 |
| | 3 | 0.2 | 1.6 | NM | NM |
| | 4 | 0.2 | 1.0 | 8.4 | 1.0 |
| | 6 | 0.2 | 0.6 | 3.1 | 0.9 |
| | 8 | 0.2 | 2.2 | 2.6 | 1.0 |
| | 10 | 0.2 | 1.2 | NM | NM |
| | 12 | 0.2 | 0.8 | NM | NM |
| | 24 | 0.1 | 0.5 | NM | NM |
| Peak serum progesterone level in ng/ml | | 0.2 | 2.4 | 8.4 | 1.0 |
| Hour peak serum level reached | | 2 | 2 | 4 | 4 |

None of these comparative samples achieved peak progesterone blood serum levels comparable to the levels achieved by the samples according to the invention.

Samples T through Z compare Utrogestan (Samples T, W, Y), micronized progesterone heat dissolved in safflower oil (Samples U, Z) with Samples V and X representing the present invention:

TABLE 7

| | Samples | | | | | | |
|---|---|---|---|---|---|---|---|
| | T | U | V | W | X | Y | Z |
| | (Patient F8) | | | (Patient F9) | | (Patient F10) | |
| 0 | 0.8 | 0 | 0.5 | 0.5 | — | 0.5 | 0.2 | 0.2 | — |
| ½ | 0.2 | 0.1 | 0.3 | 0.9 | — | 22.8 | 2.7 | 0.2 | — |
| 1 | 3.5 | 0.8 | 16.6 | 2.9 | — | 27.5 | 17.8 | 1.3 | — |
| 2 | 21.8 | 1.2 | 3.8 | 15.3 | — | 12.2 | 4.5 | 1.1 | — |
| 3 | 5.0 | 1.1 | 2.1 | 3.8 | — | 6.1 | 2.6 | 1.1 | — |
| 4 | 3.3 | 0.7 | 1.6 | 6.4 | — | 4.3 | 1.5 | 0.7 | — |
| 6 | 2.3 | 1.5 | 1.3 | 3.6 | — | 2.7 | 1.7 | 0.7 | — |
| 24 | 0.7 | 0.5 | 0.9 | 0.6 | — | 0.6 | 0.5 | 0.3 | — |

The following Table 8 summarizes the results of the averages for the French product, Utrogestan, as compared to the averages for the samples according to the invention. The results given in the column AV-1 are averages for trials F, T, W and Y employing Utrogestan. The results in the column AV-2 are averages of the results for trials J, L, V and X according to the invention. The results are as follows:

TABLE 8

| Time (Hours) | AV-1 | AV-2 |
|---|---|---|
| 0 | 0.5 | 0.6 |
| ½ | 1.1 | 6.0 |
| 1 | 6.2 | 11.4 |
| 2 | 10.8 | 10.8 |
| 3 | 3.6 | 5.3 |
| 4 | 5.1 | 3.8 |
| 6 | 2.8 | 2.3 |
| 24 | 0.7 | 1.0 |

The foregoing averages indicate that the samples according to the invention generally achieved higher peak serum levels in shorter time periods than the French product Utrogestan. Further, the average of the peak serum progesterone levels for Utrogestan (Samples F, T, W, Y) was 16.0 ng/ml, whereas the average for the Samples J, L, V and X according to the invention was 17.9 ng/ml. The foregoing results indicate the remarkable effectiveness of the present invention in comparison to similar compositions, even compositions utilizing micronized progesterone in oils such as Crisco vegetable cooking oil or mineral oil.

It will be understood that the above description is of preferred exemplary embodiments of the present invention, and the invention is not limited to the specific methods or compositions shown. Modifications may be made in the composition or method according to the invention without departing from the scope of the invention as expressed in the appended claims.

We claim:

1. A method of treating premenstrual syndrome, comprising orally administering to a woman suffering from premenstrual syndrome a therapeutically effective amount of an oral dosage form of progesterone comprising a suspension of micronized progesterone in an edible oil consisting essentially of not more than about 16 wt. % of saturated fatty acid glycerides, and the balance is essentially at least two glycerides of oleic, linoleic, and linolenic acids, said suspension being contained in a pharmacologically acceptable capsule, wherein said dosage form is administered over a period of consecutive days during the second half of the menstrual cycle between ovulation and menstruation in a dosage sufficient to increase blood serum levels of progesterone to at least 10 ng/ml.

2. The method of claim 1, wherein said oral dosage form of progesterone consists essentially of a suspension of micronized progesterone particles having particle sizes of less than about 10 microns, a majority of said particles having particle sizes of less than about 5 microns, and the amount of said oil is in the range of about 1.5 to 2.5 ml of said oil per gram of progesterone.

3. The method of claim 2, wherein said oral dosage form is administered in an amount in the range of 200 to 600 milligrams of progesterone per day.

4. The method of claim 1, wherein said oil consists essentially of glycerides of polyunsaturated fatty acids.

5. The method of claim 1, wherein said oil is corn oil.

6. The method of claim 1, wherein said oil is peanut oil.

7. The method of claim 1, wherein said oil is sunflower oil.

8. The method of claim 1, wherein said oil is soybean oil.

9. The method of claim 2, wherein said capsule contains 50 to 150 milligrams of progesterone per capsule.

10. The method of claim 6, wherein said capsule contains 90 to 110 milligrams of progesterone per capsule.

11. The method of claim 1, wherein said period is about 12 days and begins about 2 days after ovulation based on a 28 day menstrual cycle.

12. A method for preparing a pharmaceutical composition comprising micronized progesterone suspended in an edible oil, said oil comprising glycerides of one or more polyunsaturated fatty acids and dissolved progesterone, which method comprises the steps of:
 mixing a first quantity of progesterone with said oil;
 heating the resulting mixture to dissolve said first quantity of progesterone in said oil;
 cooling said mixture to a temperature sufficiently low that micronized progesterone does not dissolve in said oil;
 suspending a second quantity of micronized progesterone in said oil to form said pharmaceutical composition.

* * * * *